United States Patent [19]
Stricklin

[11] Patent Number: 5,950,620
[45] Date of Patent: Sep. 14, 1999

[54] RESUSCITATION DEVICE FOR USE WITH STOMAS

[76] Inventor: Walter D. Stricklin, 1331 W. Pikes Peak Ave., Colorado Springs, Fla. 80904

[21] Appl. No.: 09/106,394

[22] Filed: Jun. 29, 1998

[51] Int. Cl.⁶ .................................................. A61M 16/00
[52] U.S. Cl. ............................... 128/202.28; 128/202.29; 128/203.11; 128/207.16
[58] Field of Search .................. 128/202.28, 202.29, 128/203.11, 207.16, 207.29, 912, DIG. 26; 623/9

[56] References Cited

U.S. PATENT DOCUMENTS

| | | | |
|---|---|---|---|
| 2,039,142 | 4/1936 | Brehm | 128/207.16 |
| 3,137,299 | 6/1964 | Tabor | 623/9 |
| 3,407,810 | 10/1968 | Waldrep | 128/202.28 |
| 3,508,543 | 4/1970 | Aulicano | 128/202.28 |
| 4,040,428 | 8/1977 | Clifford | 128/207.16 |
| 4,325,366 | 4/1982 | Tabor | 128/207.16 |
| 4,538,607 | 9/1985 | Saul | 128/207.16 |
| 4,856,548 | 8/1989 | Paluch | 128/205.24 |
| 4,870,962 | 10/1989 | Sitnik | 128/205.24 |
| 4,886,057 | 12/1989 | Nave | 128/202.28 |
| 4,893,620 | 1/1990 | Wadwha | 128/202.13 |
| 4,971,054 | 11/1990 | Andersson et al. | 128/207.16 |
| 5,000,741 | 3/1991 | Kalt | 128/207.29 |
| 5,042,468 | 8/1991 | Lambert | 128/207.29 |
| 5,101,820 | 4/1992 | Christopher | 128/204.18 |
| 5,119,809 | 6/1992 | Gerson | 128/202.28 |
| 5,259,378 | 11/1993 | Huchon et al. | 128/207.16 |
| 5,355,877 | 10/1994 | Cheng | 128/202.28 |
| 5,386,822 | 2/1995 | Jones | 128/202.28 |
| 5,487,382 | 1/1996 | Bezicot | 128/207.16 |
| 5,606,966 | 3/1997 | Smith | 128/207.17 |
| 5,666,950 | 9/1997 | Smith | 128/207.29 |
| 5,738,095 | 4/1998 | Persson | 128/912 |
| 5,765,560 | 6/1998 | Verkerke et al. | 128/207.16 |

*Primary Examiner*—Aaron J. Lewis
*Attorney, Agent, or Firm*—Phillip A. Rein

[57] ABSTRACT

A resuscitation device for use with stomas including a shield having an aperture centrally therethrough to provide for a flow of air. A ventilation tube is provided having an open upper end secured within the aperture of the shield. The ventilation tube has a tapered lower portion terminating in an open lower end. The tapered lower portion is dimensioned for being received with a stoma of a person. A disk is positioned within the ventilation tube. A screen is secured within the open lower end of the tapered lower portion.

8 Claims, 2 Drawing Sheets

RESUSCITATION DEVICE FOR USE WITH STOMAS

BACKGROUND OF THE INVENTION

1. Field of the Invention

The present invention relates to a resuscitation device for use with stomas and particularly pertains to providing a physical barrier for use in performing mouth-to-stoma resuscitation with a resuscitation device for use with stomas.

2. Description of the Prior Art

The use of respiratory devices is known in the prior art. More specifically, respiratory devices heretofore devised and utilized for the purpose of supplying respiratory gas to another person are known to consist basically of familiar, expected, and obvious structural configurations, notwithstanding the myriad of designs encompassed by the crowded prior art which have been developed for the fulfillment of countless objectives and requirements.

By way of example, U.S. Pat. No. 3,407,810 to Waldrepp; U.S. Pat. No. 3,508,543 to Aulicono; U.S. Pat. No. 4,886,057 to Nave; U.S. Pat. No. 5,119,809 to Gerson; U.S. Pat. No. 5,355,877 to Cheng; and U.S. Pat. No. 5,386,822 to Jones.

While these devices fulfill their respective, particular objective and requirements, the aforementioned patents do not describe a resuscitation device for use with stomas for providing a physical barrier for use in performing mouth-to-stoma resuscitation.

In this respect, the resuscitation device according to the present invention substantially departs from the conventional concepts and designs of the prior art, and in doing so provides an apparatus primarily developed for the purpose of providing a physical barrier for use in performing mouth-to-stoma resuscitation.

Therefore, it can be appreciated that there exists a continuing need for a new and improved resuscitation device which can be used for providing a physical barrier for use in performing mouth-to-stoma resuscitation. In this regard, the present invention substantially fulfills this need.

SUMMARY OF THE INVENTION

In the view of the foregoing disadvantages inherent in the known types of respiratory devices now present in the prior art, the present invention provides an improved resuscitation device for use with stomas. As such, the general purpose of the present invention, which will be described subsequently in greater detail, is to provide a new and improved resuscitation device for use with stomas and method which has all the advantages of the prior art and none of the disadvantages.

To attain this, the present invention essentially comprises a shield having a generally rectangular configuration. The shield is fabricated of a transparent plastic material. The shield has an aperture centrally therethrough to provide for a flow of air. A ventilation tube is provided having an open upper end secured within the aperture of the shield. The ventilation tube has a tapered lower portion terminating in an open lower end. The tapered lowered portion is dimensioned for being received within a stoma of a person. An inner surface of the ventilation tube has an annular protrusion extending around a periphery thereof intermediate the open upper and lower ends. The tapered lower portion has a support arm extending inwardly from an inner surface thereof. A free end of the support arm has an upwardly extending support. The upwardly extending support is angularly disposed. A disk is positioned within the ventilation tube between the annular protrustion and an upper end of the upwardly extending support of the support arm. A screen is secured within the open lower end of the tapered lower portion.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved resuscitation device for use with stomas which has all the advantages of the prior art respiratory devices and none of the disadvantages.

It is another object of the present invention to provide a new and improved resuscitation device for use with stomas which may be easily and efficiently manufactured and marketed.

It is a further object of the present invention to provide a new and improved resuscitation device for use with stomas which is of durable and reliable construction.

An even further object of the present invention is to provide a new and improved resuscitation device for use with stomas which is susceptible of a low cost of manufacture with regard to both materials and labor, and which accordingly is then susceptible of low prices of sale to the consuming public, thereby making such a resuscitation device for use with stomas economically available to the buying public.

Even still another object of the present invention is to provide a new and improved resuscitation device for use with stomas for providing a physical barrier for use in performing mouth-to-stoma resuscitation.

Lastly, it is an object of the present invention to provide a new and improved resuscitation device for use with stomas including a shield having an aperture centrally therethrough to provide for a flow of air. A ventilation tube is provided having an open upper end secured within the aperture of the shield. The ventilation tube has a tapered lower portion terminating in an open lower end. The tapered lower portion is dimensioned for being received within a stoma of a person. A disk is positioned within the ventilation tube. A screen is secured with the open lower end of the tapered lower portion.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth will become apparent when consideration is given to the following detailed description thereof. Such description makes reference to the annexed drawings wherein.

The same reference numerals refer to the same parts through the various figures.

DESCRIPTION OF THE PREFERRED EMBODIMENT

Figure 1:
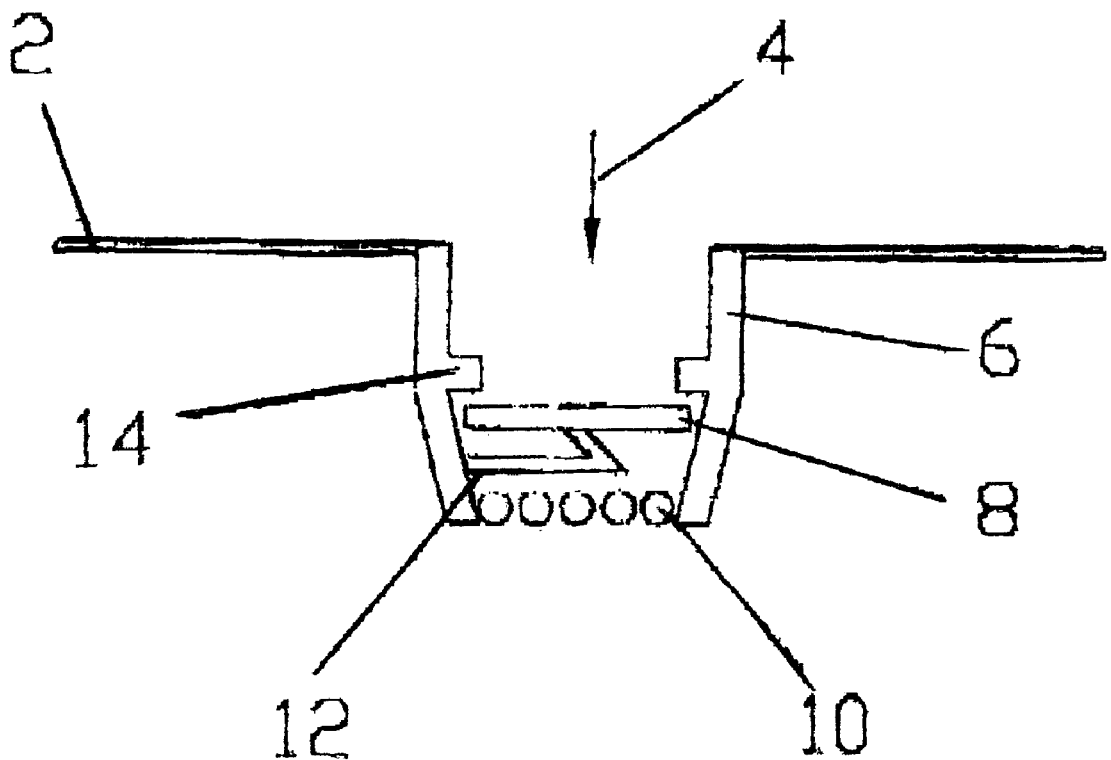
FIG. 1 is a side elevation view of the present invention illustrated in cross-section.
Figure 2:
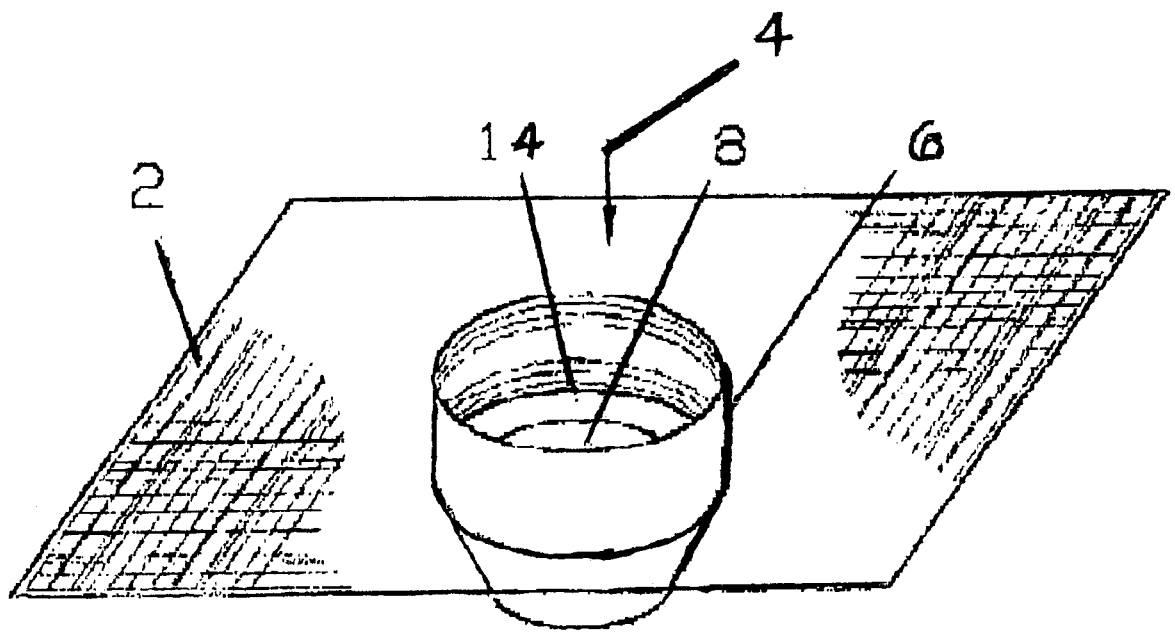
FIG. 2 is a perspective view of the preferred embodiment of the resuscitation device for use with stomas constructed in accordance with the principles of the present invention.

With reference now to the drawings, and in particular, to FIGS. 1 and 2 thereof, thereof, the preferred embodiment of the new and improved resuscitation device for use with stomas embodying the principles and concepts of the present invention and generally designated by the reference number 10 will be described.

Specifically, it will be noted in the various Figures that the device relates to a resuscitation device for use with stomas for providing a physical barrier for use in performing mouth-to-stoma resuscitation. In its broadest context, the device consists of a shield, a ventilation tube, a disk, and a screen. Such components are individually configured and correlated with respect to each other so as to attain the desired objective.

The shield 2 has a generally rectangular configuration. The shield 2 is fabricated of a transparent plastic material. The plastic material is preferably flexible. The shield 2 has an aperture centrally therethrough to provide for a flow of air 4. The shield 2 provides a physical barrier to germs and disease when placed around the stoma of a person whereby the aperture would surround the stoma. The transparency of the shield 2 allows for a rescuer to see the victim.

The ventilation tube 6 has an open upper end secured win the aperture of the shield 2. The ventilation tube 6 has a tapered lower portion terminating in an open lower end. The tapered lower portion is dimensioned for being received within a stoma of a person. An inner surface of the ventilation tube 6 has an annular protrusion 14 extending around a periphery thereof intermediate the open upper and lower ends. The tapered lower portion has a support arm 12 extending inwardly from an inner surface thereof. A free end of the support arm 12 has an upwardly extending support. The upwardly extending support is angularly disposed.

The disk 8 is positioned within the ventilation tube 6 between the annular protrusion 14 and an upper end of the upwardly extending support of the support arm 8. The disk 8 lays at rest under the annular protrusion 14, essentially level with respect to the ventilation tube 6. Once air flow pressure is applied through the open upper end of the ventilation tube 6, the disk 8 will move down against the support arm 12. As the disk 8 drops against the support arm 12 the angular orientation of the upwardly extending support will cause the disk 8 to urge towards one side on the ventilation tube thereby allowing the air to flow through the tube 6 into the stoma opening. If the flow of air should reverse, the pressure will reverse the direction of the disk 8 which will abut the annular protrusion 14 to effect a seal that will protect a rescuer from foreign matter or disease from the stoma victim.

The screen 10 is secured within the open lower end of the tapered lower portion of the ventilation tube 6. The screen 10 would protect the rescuer from any particulate that would back flow from the stoma victim during resuscitation As to the manner of usage and operation of the present invention, the same should be from the above description. Accordingly, no further discussion relating to the manner of usage and operation will be provided.

With respect to the above description then, it is to be realized that the optimum dimensional relationships for the parts of the invention, to include variations in size, materials, shape, form, function, and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, accordingly, all suitable modification and equivalents may be resorted to, falling within the scope of the invention.

What is claimed as being new and desired to be protected by Letters Patent of the U.S. is as follows:

1. A resuscitation device for use with stomas for providing a physical barrier for use in performing mouth-to stoma resuscitation comprising, in combination:

a) a shield having a generally rectangular configuration, the shield being fabricated of a transparent plastic material, the shield having an aperture centrally therethrough to provide for a flow of air;

b) a means for performing mounth-to-stoma resuscitation including a ventilation tube having an open upper end secured within the aperture of the shield, the ventilation tube having a tapered lower portion terminating in an open lower end, the tapered lower portion being dimensioned for being received within a stoma of a person, an inner surface of the ventilation tube having an annular protrusion extending around a periphery thereof intermediate the open upper and lower ends, the tapered lower portion having a support arm extending inwardly from an inner surface thereof, a free end of the support arm having an upwardly extending support, the upwardly extending support being angularly disposed;

c) a disk positioned within the ventilation tube between the annular protrusion and an upper end of the upwardly extending support of the support arm; and d) a screen secured within the open lower end of the tapered lower portion of the ventilation tube.

2. A resuscitation device for use with stomas for providing a physical barrier for use in performing mouth-to-stoma resuscitation comprising, in combination:

a) a shield for having an aperture centrally therethrough to provide a flow of air;

b) means for performing mouth-to-stoma resuscitation including a ventilation tube having an open upper end secured within the aperture of the shield, the ventilation tube having a tapered lower portion terminating in an open lower end, the tapered lower portion being dimensioned for being received within a stoma of a person;

c) a disk positioned within the ventilation tube;

d) a screen secured within the open lower end of the tapered lower portion of the ventilation tube; and e) an inner surface of the ventilation tube has an annular protrusion extending around a periphery thereof intermediated the open upper and lower ends, the tapered lower portion having a support arm extending inwardly from an inner surface thereof, a free end of the support arm having an upwardly extending support, the upwardly extending support being angularly disposed whereby the disk is positioned within the ventilation tube between the annular protrusion and an upper end of the upwardly extending support of the support arm.

3. A resuscitation device for use with stomas for providing a physical barrier for use in performing mouth-to-stoma resuscitation comprising, in combination:

a) a shield having an aperture therethrough to provide for a flow of air;

b) means for performing mouth-to-stoma resuscitation including a ventilation tube having an open upper end secured with the aperture of the shield, the ventilation tube having a lower portion terminating in an open lower end, the lower portion being dimensioned for being received within a stoma of a person, an inner surface of the ventilation tube having an annular protrusion extending around a periphery thereof between the open upper and lower ends, the tapered lower portion having a support arm extending inwardly from an inner surface having a free support end; and c) a disk positioned within the ventilation tube between the annular protrusion and the free support end of the support arm.

4. The resuscitation device as described in claim 3, wherein:

a) the aperture positioned centrally of the shield; and b) the lower portion being tapered for being received within the stoma of a stoma victim.

5. The resuscitation device as described in claim 3, including:

a) a screen secured within the outer end of the ventilation tube to prevent any particulate matter from backflowing from a stoma victim to a resuscitator during resuscitation.

6. The resuscitation device as described in claim 3, wherein:

a) the ventilation tube includes an inner surface of the annular protrusion having a sealing surface;

b) the disk abuts the seating surface to prevent fluid and particulate flow to the resuscitator from a stoma victim; and c) the disk abuts the free support end of the support arm to allow air flow to the stoma victim;

whereby the disk acts as a one-way air flow valve.

7. The resuscitation device as described in claim 6, wherein:

a) the free support end being angularly disposed relative to an outer portion of the support arm; and b) an outer tip of the free support end contacts an outer central portion of the disk to hold in a level, spaced parallel relationship relative to the sealing surface on the annular protrusion to allow air flow to pass the disk to the stoma victim.

8. The resuscitation device as described in claim 3, wherein:

a) the shield constructed of a flexible, transparent material to allow the resuscitator to observe the condition of the stoma victim; and b) the shield extends substantially laterally of the ventilation tube to protect a resuscitator from particulate matter discharged from a stoma victim.

* * * * *